United States Patent [19]

Liu et al.

[11] 4,170,639
[45] Oct. 9, 1979

[54] ANTIHEMOPHILIC FACTOR CONCENTRATE AND ITS PRODUCTION

[75] Inventors: Daniel T. H. Liu, Troy; John F. Irwin, Grosse Pointe Park; Rong-Chang Pai, Troy, all of Mich.

[73] Assignee: Warner-Lambert Company, Morris Plains, N.J.

[21] Appl. No.: 923,139

[22] Filed: Jul. 10, 1978

[51] Int. Cl.$^2$ .............................................. A61K 35/16
[52] U.S. Cl. ..................................................... 424/101
[58] Field of Search ......................................... 424/101

[56] References Cited

U.S. PATENT DOCUMENTS

| 3,652,530 | 3/1972 | Johnson | 424/101 |
| 3,973,002 | 8/1976 | Hagan | 424/101 |
| 4,087,415 | 5/1978 | Bick et al. | 424/101 |
| 4,093,608 | 6/1978 | Iga et al. | 424/101 |

OTHER PUBLICATIONS

Swart et al.—Chem. Abst., vol. 77 (1972) p. 124,372g.

Primary Examiner—Sam Rosen
Attorney, Agent, or Firm—David B. Ehrlinger; Stephen Raines; Frank S. Chow

[57] ABSTRACT

Antihemophilic factor (AHF) concentrate having enhanced potency and solubility and its process of production are provided. The process includes the steps of removing unwanted protein from an aqueous extract of antihemophilic blood plasma cryoprecipitate by mixing the aqueous extract with aluminum hydroxide at an acid pH in the cold, adjusting the purified aqueous extract to an acid pH and freeze-drying the extract, optionally removing water from the extract just before freeze-drying.

10 Claims, No Drawings

ANTIHEMOPHILIC FACTOR CONCENTRATE AND ITS PRODUCTION

SUMMARY AND DETAILED DESCRIPTION

The present invention relates to antihemophilic factor (AHF) concentrate having enhanced potency and solubility, and to a process for its production in which unwanted protein is removed at an acid pH from an aqueous extract of antihemophilic blood plasma cryoprecipitate, the purified extract is constituted with buffer and saline and adjusted to an acid pH, and the adjusted extract is freeze-dried, optionally after water removal.

In conventional practice, AHF concentrate having intermediate purity is obtained from plasma. This is done by thawing frozen plasma, obtaining the cryoprecipitate, extracting AHF from the cryoprecipitate with water or aqueous buffer, and further purifying the aqueous extract by removal of unwanted protein at neutral pH.

The procedure, using aluminum hydroxide as an adsorbent, is described by James et al., Vox Sang. 23:402–412, and Hershgold et al., J. Lab. Clin. Med. 67:23–32, which description is incorporated herewith by reference. The resulting intermediate purity AHF concentrate is constituted with buffer and saline at neutral pH and distributed in freeze-dried powder form. It is used as an injectable liquid (reconstituted just prior to administration by dissolving in water) for intravenous administration to hemophilic patients. The conventional powder concentrate typically has a reconstitution time of about 4 minutes or more at 23° C. (about 2.5 minutes or more at 37° C.) and in liquid form has a potency of 25–30 AHF units per milliliter.

A more potent concentrate—the so-called highly purified or high potency AHF concentrate—is obtained by further purification, for example, purification with polyethylene glycol (PEG) or glycine. For a description of the procedure, see Hershgold et al., supra, and Newman et al., Brit. J. Haem. 21:1–20. Although highly purified AHF concentrate has the advantage of high potency and good solubility, the yield is less than that obtained for intermediate purity AHF concentrate. In fact, the loss in yield due to the added fractionation step using alcohol, PEG or glycine is reported to be from 20 to 35% or more.

The art thus offers a choice between the AHF product having intermediate purity produced in good yield or the highly purified high potency AHF product produced in lower yield.

The object of the present invention is therefore to provide AHF concentrate in purified form having enhanced potency and solubility, and, further, to provide an economical process for its production.

It is also an object to provide a process for the production of high potency AHF concentrate which avoids the loss of yield of the magnitude associated with conventional processes.

These and other objects, advantages and features will appear from the following description and specification of the invention.

According to the present invention, AHF concentrate in purified form having enhanced potency and solubility is provided by a process comprising the steps of subjecting an aqueous extract of antihemophilic blood plasma cryoprecipitate to purification by mixing with an aluminum hydroxide adsorbent at an acid pH and precipitating in the cold, the pH conditions being such that unwanted protein is selectively removed by adsorption without substantial loss of antihemophilic factor potency from the aqueous extract, constituting the purified aqueous extract with buffer and saline and adjusting to an acid pH, and freeze-drying the thus adjusted aqueous extract, optionally after removal of water from the extract by means of a semi-permeable membrane or ultrafiltration.

The resulting product has good AHF activity and, by comparison with the prior art product obtained by purification at neutral pH, has significantly improved characteristics such as shorter reconstitution time and a lower content of clottable protein (i.e., unwanted protein). Also, the product obtained through use of the optional water removal step likewise has superior characteristics such as excellent solubility on reconstitution and markedly improved stability of AHF activity in the reconstituted solution form. As indicated, the instant process in the steps of purification and constituting with buffer and saline, is carried out at an acid pH. For purposes of the invention, an acid pH is a pH or pH range lower than neutrality, preferably between about 6.55 to about 6.8. The various assay measurements of the product can be done by conventional methods. The AHF activity or potency is suitably measured by the partial thromboplastin time (PTT) assay, Proctor et al., Amer. J. Clin. Path. 36:212. Protein concentration using bovine albumin as a standard is conveniently measured by the biuret method, Gornall et al., J. Biol. Chem. 177:751. Clottable protein is determined as the difference in total protein measured before and after thrombin-induced clotting of fibrinogen. The materials used in the instant process, of which the following preferred embodiments are illustrative, are available from commercial sources. The aluminum hydroxide gel (F-500, Reheis Co.) containing 0.1446 grams of aluminum hydroxide per gram of gel in one preferred form is made up for use as a 10% by weight gel suspension in distilled water. A buffer solution—0.4 M phosphate, pH 5.8, buffer—is prepared by adding 460 grams of monobasic sodium phosphate, monohydrate, and 94.6 grams of dibasic sodium phosphate, anhydrous, to distilled water and making up to 10 liters. The equipment used for centrifugation, freeze-drying and water removal (ultrafiltration) is conventional.

The process of the invention is illustrated by the following preferred embodiment:

Preparation of Cryoprecipitate (a) Fast frozen fresh antihemophilic factor plasma, hepatitis-negative, is quickly thawed to 0° to 2° C. (each ml. typically containing about 0.75 AHF units and about 60 mg. of protein) in a jacketed tank circulated with warm ethylene glycol. Sufficient 95% 3A alcohol is added to the cold plasma to make a concentration of 0.5% alcohol by weight. The thawed plasma is then centrifuged at 2° to 6° C. in a Sharples centrifuge. The bowl cake (cryoprecipitate or cryoprotein) is collected and retained for preparation of AHF.

Extraction, pH Adjustment and Purification (b) A 100-gram aliquot of the cryoprecipitate product of paragraph (a) is minced and suspended in 400 ml. of water. The pH is adjusted to 7.0 to 7.1 with 0.1 N hydrochloric acid solution. The mixture is centrifuged, and the effluent aqueous extract is collected and readjusted to pH 6.8 with 0.1 N hydrochloric acid. The protein content is determined and the equivalent of 0.01 grams of aluminum hydroxide (as a 10% suspension of gel) is added per gram of protein, while maintaining the pH of the aqueous extract at 6.8. After mixing at room temperature, the suspension is cooled to 4° C. and held for 1½ to 2 hours. The cold suspension is centrifuged, the bowl cake is discarded, and the purified aqueous extract is collected.

Salination, Buffering and pH Adjustment (c) The purified aqueous extract produced by the procedure of paragraph (b) is constituted with 5.0 molar aqueous sodium chloride solution (the latter being added in the proportion of six parts to each 964 parts by volume of the extract). Phosphate buffer solution (0.4 M, pH 5.8, described above) is added in the proportion of 10 ml. for each liter of salinated extract. The pH of the mixture is then adjusted to 6.65 to 6.75 with 0.1 N aqueous hydrochloric acid solution. The mixture is stirred while maintaining the pH at 6.65 to 6.75. The resulting pH-adjusted aqueous extract is filtered to remove particles and then sterile filtered through a series of three membranes with respective average pore sizes of 1.2, 0.45 and 0.22 microns. The filtrate is assayed for bulk sterility and AHF potency.

Water Removal (Ultrafiltration)

(d) As an optional step, for the removal of water, the purified aqueous extract of paragraph (c) may be concentrated by ultrafiltration using a semi-permeable membrane prior to freeze-drying described in what follows under paragraph (e). For this purpose, the extract is processed aseptically through a high-yield hollow fiber dialyzer/concentrator (Model DC30, Amicon Corp., Lexington, Mass. 02173) using 25 pounds per square inch (gauge) positive nitrogen pressure and three ultrafiltration hollow fiber membrane cartridges each having a one-million molecular weight cut-off. The extract thus processed is typically concentrated 2 to 4 folds and collected as the retentate. Another suitable unit for this purpose is the hollow fiber dialyzer/concentrator Model DC 2, Amicon Corp., using a membrane having a one-million molecular weight cut-off or the Millipore ® molecular filtrate cassette system (Millipore Corp., Bedford, Mass. 01730) in the single pass mode at 25 psig using a Series PSVP membrane cassette having a one-million nominal molecular weight limit (nmwl).

Freeze-Drying (e) An aliquot (40 ml.) of either the purified aqueous AHF extract produced by the procedure of paragraph (c) or the further concentrated extract of paragraph (d) is filled aseptically into each of the number of 50-ml. vials. The filled vials are quick-frozen in liquid nitrogen and the frozen vials lyophilized under high vacuum in a freeze-dryer chamber for 96 hours. The initial shelf temperature typically is −40° C. and the terminal temperature is 28°±2° C. The vials are then sealed in vacuum and the vacuum in the chamber broken with filtered dry nitrogen. The sterile vials thus sealed can be kept at 4° C. under ordinary conditions until required for use. For parenteral administration as an injectable liquid, the contents of the individual vial are reconstituted in 10 ml. of sterile water either at room temperature (23° C.) or at 37° C. in a water bath. The AHF concentrate of the invention thus reconstituted is superior in various ways to the conventional AHF concentrate having intermediate purity. This is illustrated by the following comparison.

Properties of AHF Concentrates on Reconstitution

|  | Conventional AHF Concentrate* | Improved AHF Concentrate* [Example Prepared as in Steps a), b), c), and e)] |
| --- | --- | --- |
| Reconstitution time (min.) | | |
| at 23° C. | 4.0 | 2.1 |
| at 37° C. | 2.3 | 1.7 |
| AHF (U/vial) | 295 | 290 |
| Potency (U/ml.) | 29.5 | 29.0 |
| Protein (mg./vial) | 426 | 341 |
| Clottable Protein (%) | 55 | 50 |
| Specific Activity (U/mg.) | 0.65 | 0.78 |
| Recovery (U/L. plasma) | 269 | 263 |
| Purification over plasma (fold) | 41 | 49 |
| pH | 7.80 | 7.03 |
| Percent AHF after 24 hours at room temperature (23° C.) | 80 | 94 |

*Average of seven lots.

These results show that the AHF concentrate of the invention has a shorter reconstitution time, a higher specific activity and less clottable protein, and is relatively more stable after reconstitution.

In separate experiments, high potency AHF concentrate prepared as described in the above example steps (a) to (e) including 2- to 4-fold concentration by water removal, typically has the several advantages of AHF concentrate of intermediate purity as shown by the following tabulation:

| Properties of High-Potency AHF | | | | |
| --- | --- | --- | --- | --- |
| Folds Concentration | 2 | 3 | 3.5 | 4 |
| Units/Vial | 510 | 656 | 746 | 928 |
| Solubility Time at 23° C. (Min.) | 2 | 2 | 3 | 3 |
| Reconstitution Volume (Ml.) | 10 | 10 | 10 | 20 |
| Total Protein (Mg.) | 490 | 827 | 848 | 816 |
| Clottable Protein (Mg.) | 220 | 415 | 408 | 339 |
| % Clottable Protein (Mg.) | 45 | 50 | 48 | 42 |
| Specific Activity (Units/Mg. Protein) | 1.04 | 0.79 | 0.88 | 1.13 |
| Yield (Units/L. Plasma) | 223 | 168 | 177 | 165 |
| # Experiment | 1 | 2 | 1 | 2 |

It is significant that as to the high potency AHF concentrate the good solubility time (2 to 3 minutes) is achieved only by the combination of pH control and water removal according to the invention; AHF concentrate made by the conventional method and concentrated by water removal typically has a much prolonged solubility time (6 to 10 minutes).

While the invention has been set forth in considerable detail, it will be realized that the invention is subject to considerable variation in such detail without departing from the scope of the invention as hereinafter claimed.

We claim:

1. Process for the production of antihemophilic factor concentrate in purified form having enhanced potency and solubility comprising the steps of (a) subjecting an aqueous extract of antihemophilic blood plasma cryoprecipitate to purification by mixing with an aluminum hydroxide adsorbent at an acid pH and precipitating unwanted protein in the cold, the pH conditions being such that unwanted protein is selectively removed by adsorption without substantial loss of antihemophilic factor potency from the aqueous extract, (b) constituting the purified aqueous extract with buffer and saline and adjusting to an acid pH, and (c) freeze-drying the thus adjusted aqueous extract.

2. Process according to claim 1, where the purification is done in the pH range between about 6.55 to about 6.8.

3. Process according to claim 1, where the purified aqueous extract is adjusted to the pH range between about 6.55 and about 6.8.

4. Process according to claim 1, where the adjusted aqueous extract is concentrated by removal of water prior to the freeze-drying step.

5. Process according to claim 4, where the water is removed by subjecting the aqueous extract to ultrafiltration.

6. Process according to claim 5, where the water is removed by means of a semi-permeable membrane.

7. Process according to claim 1 where the purified aqueous extract is constituted with buffer and saline and is adjusted to the pH range between about 6.55 and about 6.8, and, prior to the freeze-drying step, the thus adjusted aqueous extract is concentrated by ultrafiltration.

8. Antihemophilic factor concentrate produced by the process of claim 1.

9. Antihemophilic factor concentrate produced by the process of claim 4.

10. Antihemophilic factor concentrated produced by the process of claim 5.

* * * * *